United States Patent [19]
Dupree et al.

[11] Patent Number: 4,632,562
[45] Date of Patent: Dec. 30, 1986

[54] SPERM DENSIMETER

[75] Inventors: James N. Dupree, South El Monte; Jack E. Peterson, West Covina, both of Calif.

[73] Assignee: Dupree, Inc., Chino, Calif.

[21] Appl. No.: 764,099

[22] Filed: Aug. 9, 1985

Related U.S. Application Data

[62] Division of Ser. No. 605,123, Apr. 30, 1984.

[51] Int. Cl.$^4$ ............................................. G01N 21/00
[52] U.S. Cl. .................................... 356/436; 356/442; 250/364
[58] Field of Search ............................... 356/432–442; 250/564–565, 573–576; 377/29, 11

[56] References Cited

U.S. PATENT DOCUMENTS 3,807,875  4/1974  Fischer et al. .................... 356/432
3,944,797  3/1976  Coulter et al. .................... 377/11 X
4,176,953 12/1979  Bartoov et al. ................... 356/436 X Primary Examiner—R. A. Rosenberger
Attorney, Agent, or Firm—Harris, Kern, Wallen & Tinsley

[57] ABSTRACT

Apparatus and method for measuring the density of sperm in a sample and for calculating the magnitude of dose required for artificial insemination. An optical assembly with light source, specimen holder and photodetector providing a signal to an amplifier the output of which is proportional to absorbance of the sample. A signal selection system utilizes three parallel signal channels with each having a different correction factor for matching the absorbance signal to actual density count, and including means for selecting the appropriate signal channel as a function of signal amplitude, with the output when calibrated providing the direct reading of the sperm density. Knowing the number of sperm cells desired per insemination and the percent motility of the sample sperm, the required dose is calculated as a function of the density count.

7 Claims, 4 Drawing Figures

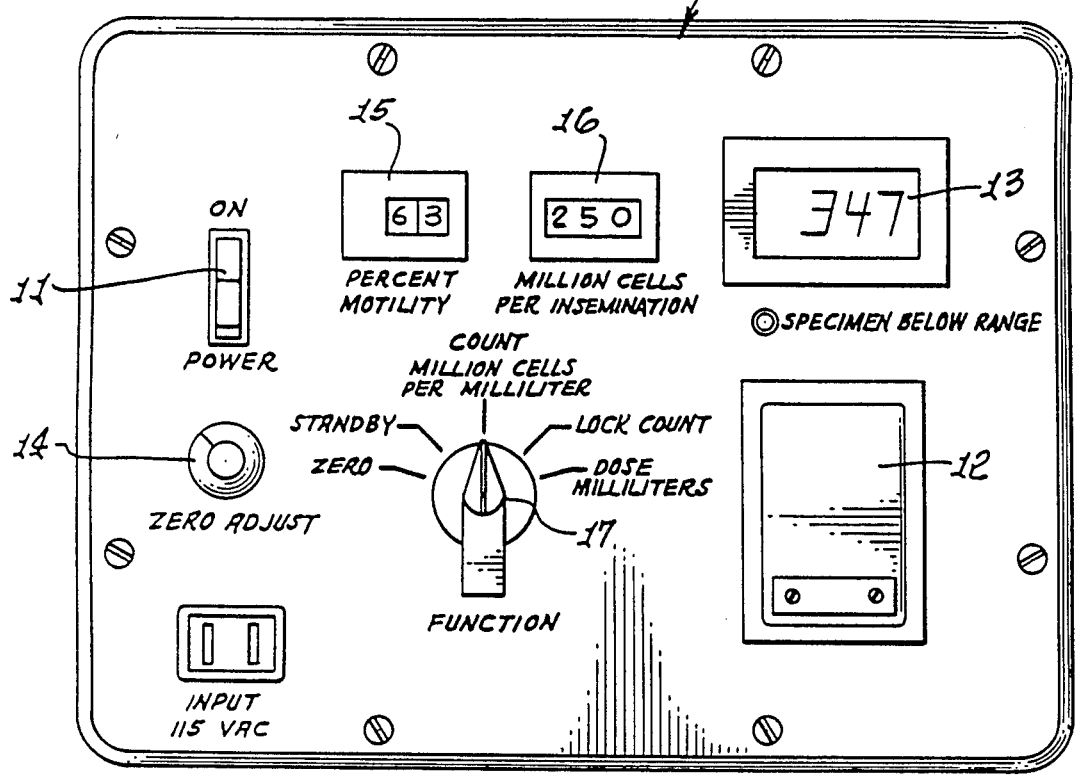
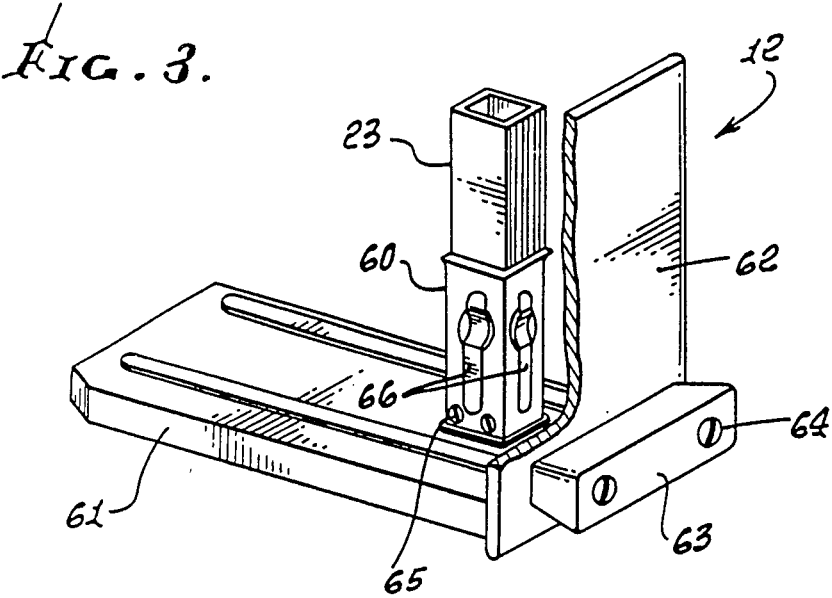

SPERM DENSIMETER

This application is a division, of application Ser. No. 605,123, filed Apr. 30, 1984.

This invention relates to new and improved apparatus and method for the measurement of the sperm density in a specimen and the determination of dosages for artificial insemination.

When properly practiced, artificial insemination (AI) can be a highly successful management technique for improving the reproductive efficiency of various domestic animals.

AI is widely practiced in the cattle breeding industry; is finding increasing use in equine (all breeds except thoroughbred) reproduction; and is being used, at least experimentally in the breeding of canines and other animals.

There are many specific reasons for the practice of AI, most of which ultimately reduce to a matter of economics. For example, an AI program conducted by competent practitioners using proven techniques and equipment can reduce the occurrence of injury to valuable animals and diminish the transmission of certain reproductive system diseases. Additionally, and of major importance, a maximum number of females can be brought into pregnancy in minimum time and the number of progeny from males of recognized genetic superiority can be greatly increased.

Although the detailed procedures and the apparatus used in an AI program vary with the characteristics and anatomy of the various species, the handling, processing and evaluation of semen in the field laboratory is nearly the same for all animals.

It is important that the semen be protected from sunlight and that it be held at nearly constant animal body temperature from the time that it is collected until insemination is accomplished. All apparatus and containers that will come into contact with any semen that is to remain viable must be clean, warmed before use and held at constant temperature wherever possible. In some species, such as the equine, the ejaculate contains a gel-like substance which has no bearing on fertility but does interfere with laboratory evaluation and insemination procedures. The gel is usually removed at the time of collection by passing the ejaculate through an appropriate filter mesh prior to its entry into the holding container. Ideally, semen which has been properly collected from a healthy animal is essentially free of gel and contaminants and consists only of spermatozoa suspended in a clear plasma.

A sample of uniform mix of the collected semen is drawn for laboratory analysis during which time the bulk of the semen is stored in a properly regulated incubator. Even under the best of storage and handling conditions, various changes and a gradual deterioration in the quality of the semen will occur over a period of time. The rate of deterioration differs as time progresses and tends to be greater in the laboratory sample than in the incubated semen.

The laboratory work, then, must be conducted with great care yet be accomplished as rapidly and efficiently as possible to assure good correlation between the laboratory measurements and stored semen and provide inseminating fluid of the highest possible potency.

The laboratory evaluation of the semen may be quite sensitive. However, in routine work a minimal evaluation may be all that is required. A minimal evaluation includes at least the following points:

1. An initial visual and olfactory examination to appraise semen quality and detect the presence of contaminants (dirt, urine, blood, etc.). 2. A measurement of the total volume of ejaculate.

3. An estimate of semen fertility.

4. A determination of the spermatozoa concentration or density (number of sperm cells per unit volume).

5. A calculation of the total number of sperm cells per ejaculate.

6. A determination of the volume of gel-free semen needed for each insemination.

Items 1 and 2, sensory evaluation and measurement of volume require an additional comment for purposes of this application.

Item 3, estimation of sperm fertility, is accomplished by a subjective microscopic examination of a standardized dilution of semen to determine the percentage of sperm that are viable. In routine practice, this is done by observing the motility patterns of the spermatozoa and estimating the percentage that move in a typical progressive or forward manner. Other types of movement that have been categorized are circular, vibratory, reverse and flagellating. These movement patterns are thought to be indicative of sperm cells that are unlikely to be capable of achieving ovum fertilization. A more detailed evaluation is sometimes used which includes a study of cell morphology under high power magnification. The extent to which the sample is free of cells having certain physical deformities which are thought to affect fertility may be used to refine the fertility rating.

Item 4, determination of spermatozoa density, may be accomplished by any of the several different methods, four of which are: (1) estimation based upon visual observation of semen turbidity under standardized conditions; (2) visual count using a microscope and hemocytometer; (3) electronic counting and (4) photoelectric techniques in which a measured optical parameter of a standardized sample is correlated to sperm cell density.

Each method has particular advantages and disadvantages. Visual estimation is rapid and inexpensive but yields the poorest accuracy. Hemocytometer counts can be accurate but are tedious and time consuming. Properly performed electronic counting using modern instrumentation probably provides the highest accuracy but the equipment is expensive and the technique seems better suited to laboratory research and to the gathering of calibration data than to practical field use. Photoelectric instrumentation appears to offer the best compromise when factors of accuracy, rapidity of measurement, required operating expertise, cost and equipment portability are all considered and therefore has received a high degree of acceptance.

Item 5, total sperm per ejaculate, is simply the product of ejaculate volume and sperm density. This is generally considered to be the best numerical indication of semen quality.

Calculation of the volume of gel-free semen needed for each insemination, item 6, is done by substituting measured and selected values into a simple equation as follows:

$$D = N/CM$$

Where

D=Dose or volume of semen in milliliters (ml) to be used for insemination.

N=Total number of viable spermatozoa desired for insemination in millions.

C=Measured concentration or density of sperm in millions of cells per ml.

M=Estimated percentage of sperm that are viable (usually percent forward motility) expressed as a decimal fraction.

The total number of viable sperm cells desired for insemination, N, is the minimum number estimated to yield a high probability of achieving ovum fertilization. The selected quantity depends upon the species of animal, any knowledge of the probable degree of fertility of a particular female (from previous experience), and the expertise and judgement of the AI practitioner. As an example, the selected total number of viable sperm cells for insemination of a mare would normally fall within the range of 100 million to 500 million.

The sperm cell concentration or density, C, and the percent forward motility, M, are both taken from data gathered in the laboratory analysis of the collected semen.

A review of the six steps required for a minimal evaluation of the collected semen shows that most are simple measurements or calculations or are subjective evaluations. Only two items require or lend themselves to the use of sophisticated instrumentation as a means of improving the rapidity and accuracy of semen evaluation. One of the items, estimation of semen fertility, can be enhanced through the use of a high quality phase-contrast type microscope. The evaluation, of course, remains subjective. As alluded to earlier, the second item that can be instrumented is the measurement of spermatozoal density. A photoelectric method for estimating sperm concentration in semen was first reported in 1939 by Comstock and Green for the ram.

Several scientific studies have since been made by other investigators to determine the relationship between the sperm concentration of various domestic animals and such photometric parameters as light scattering (or haze), transmission and absorbance. Both duplicate hemacytometer counts and electronic counting have been used to establish the independent variable.

Before measurement, the semen is diluted by a standardized ratio. Various diluents have been used, most consisting of distilled water with a small percentage of sodium citrate or sodium chloride to balance osmotic pressures on the sperm cells. In addition, some investigators have advised the inclusion of formalin to kill and fix the spermatozoa. The standardized ratio of semen to diluent is initially determined by experiment. It is dependent upon the average semen turbidity of the species and the type of instrument to be used. The dilution ratio is chosen to optimize the spread of readings over the usable range of the selected instrument.

The investigations revealed that no photometric parameter could be considered a truly linear function of sperm concentration over the full gamut of densities that might be encountered. However, for several species absorbance was discovered to be tolerably linear over a rather wide practical range of median concentrations, with slope changes being evident usually toward both extremes of the scale. Acceptable accuracy could often be achieved by assuming a linear relationship for a practical range of values followed by smoothing the measurement deviations by using a linear least squares regression analysis to derive a best-fit calibration equation.

A technique that has been devised to provide improved accuracy where needed is to specify two (or more) dilution ratios with corresponding linear regression equations. In effect, this forms multiple overlapping ranges with a portion of each range falling over the most linear segment of the instrument characteristic. A subjective evaluation of semen turbidity is then used to select the dilution ratio-equation set that will optimize the measurement accuracy.

Another research finding was that the dominant radiation wavelength used for absorbance measurement is not a critical factor, at least over the range of the visible spectrum (380 nm to 760 nm). Absorbance simply decreases in a smooth and fairly gradual manner as wavelength is increased. This indicates that any wavelength of convenience (or even a wide band of wavelengths) may be used providing that measurements are made under the same conditions that were established for calibration of the instrument.

For a number of years, objective measurements of sperm concentration have been successfully accomplished in the field using specially calibrated general purpose laboratory spectrophotometers. Most of the instruments in use are analog types which were primarily designed for measurement of percent transmission of light through test samples at a selected (narrow band) wavelength. The more modern of these instruments include an absorbance scale which is logarithmically related to percent transmission (absorbance equals 2 minus $\log_{10}$ of the percent transmission). Because a linear transmission scale can usually be interpolated and read more accurately than a non-linear absorbance scale, many of the operational procedures in use are based upon measurement of transmission. Conversion to absorbance is accomplished mathematically by the operator or, more conveniently, may be part of a computerized program if the sperm density value is taken from computer-derived graphs or charts showing transmission as the independent variable.

An investigation of prior instruments was conducted, but no existing photometer was found to have overall characteristics that would make it particularly suited for use in the determination of sperm density. Accordingly it is an object of the present invention to provide a photometer and associated components which will provide an objective measurement of sperm concentration and which can be used in the field to determine dosages. An additional object is to provide apparatus and method which will eliminate or minimize recognized deficiencies in existing systems and to provide improved accuracy and operating convenience.

It is an object of the invention to provide an instrument which functions on the basis of a direct absorbance measurement to eliminate any requirement for mathematical conversion from transmission and to allow standardization of the specimen cuvette with a single adjustment. Transmission measurements require separate adjustments for zero and full scale.

Further objects of the invention include:

a direct digital readout of sperm density to eliminate the need for the use of graphs and charts;

an automated system for optimizing measurement accuracy at low, median and high density counts with the use of only one specified dilution ratio for all measurements;

a "SPECIMEN BELOW RANGE" indicator coupled with a forced zero panel display for densities that are impractically low or below the calibrated range of the instrument;

an insemination dose computer featuring automatic entry of sperm density, digital thumbwheel entry of percent motility and total sperm per insemination, and automatic solution of the dose equation with digital display of the required dose.

It is an additional object of the invention to provide such an instrument having high reliability and one which will operate with infrequent calibration and function within specifications over an ambient temperature range of 20° F. to 110° F., and one in which the calibration procedure is straightforward with all adjustments being independent and non-iterative.

Other objects, features and results will more fully appear in the course of the following description and claims.

SUMMARY OF THE INVENTION

The apparatus of the invention provides for measuring density of sperm in a sample and includes an optical assembly providing a photodetector output to an amplifier which has been standardized to a specimen cuvette by means of an adjustable reference signal and which provides an absorbance output signal substantially proportional to light absorbance of the sample in the specimen holder in the optical assembly. The preferred embodiment of the apparatus includes three parallel signal channels, each incorporating an amplifier having the absorbance output signal as an input and each including means for adjusting the slope and vertical offset of the output of the channel with respect to the input thereto. The apparatus also includes channel selector means for selecting one of the channels as a function of the amplitude of the absorbance output signal, and means for displaying the selected output to provide a direct reading of density. The preferred embodiment also includes a means for computing a dose figure utilizing manually set cell numbers and percent motility and the measured density.

The preferred embodiment utilizes a wide band radiation spectrum in the visible range in the optical assembly, with defocused and scattered light at the photodetector.

The invention also includes a method of making the density measurement and a method of computing the necessary dose.

In the preferred embodiment of the method of the invention, the optical absorbance of a specimen cuvette containing a known amount of clear diluent is standardized to zero by means of an adjustable reference. Then a known amount of semen is uniformly mixed with the diluent and an analog signal proportional to the absorbance of the dilute sample is developed which varies as a function of the sperm density in the sample. The slope and vertical offset of this analog absorbance signal are adjusted in at least three different modes to provide for curve fitting of density measurement and actual density count. The level of the analog absorbance signal is used to select one of the modes which is then utilized as the count signal to provide the count figure for display.

The preferred embodiment of the method also provides for calculation of the necessary dose. Preferably this is accomplished by setting a desired total viable cell number for the insemination, a percent motility figure for the sample being utilized, and using these two set figures in conjunction with the measured count to calculate the dose.

BRIEF DESCRIPTION OF THE DRAWINGS

FIG. 1 is a front view of a sperm densimeter and dose calculator incorporating the presently preferred embodiment of the invention;

FIG. 3 is a perspective view of the specimen drawer of FIG. 1.

DESCRIPTION OF THE PREFERRED EMBODIMENTS

Front Panel

Figure 2A:
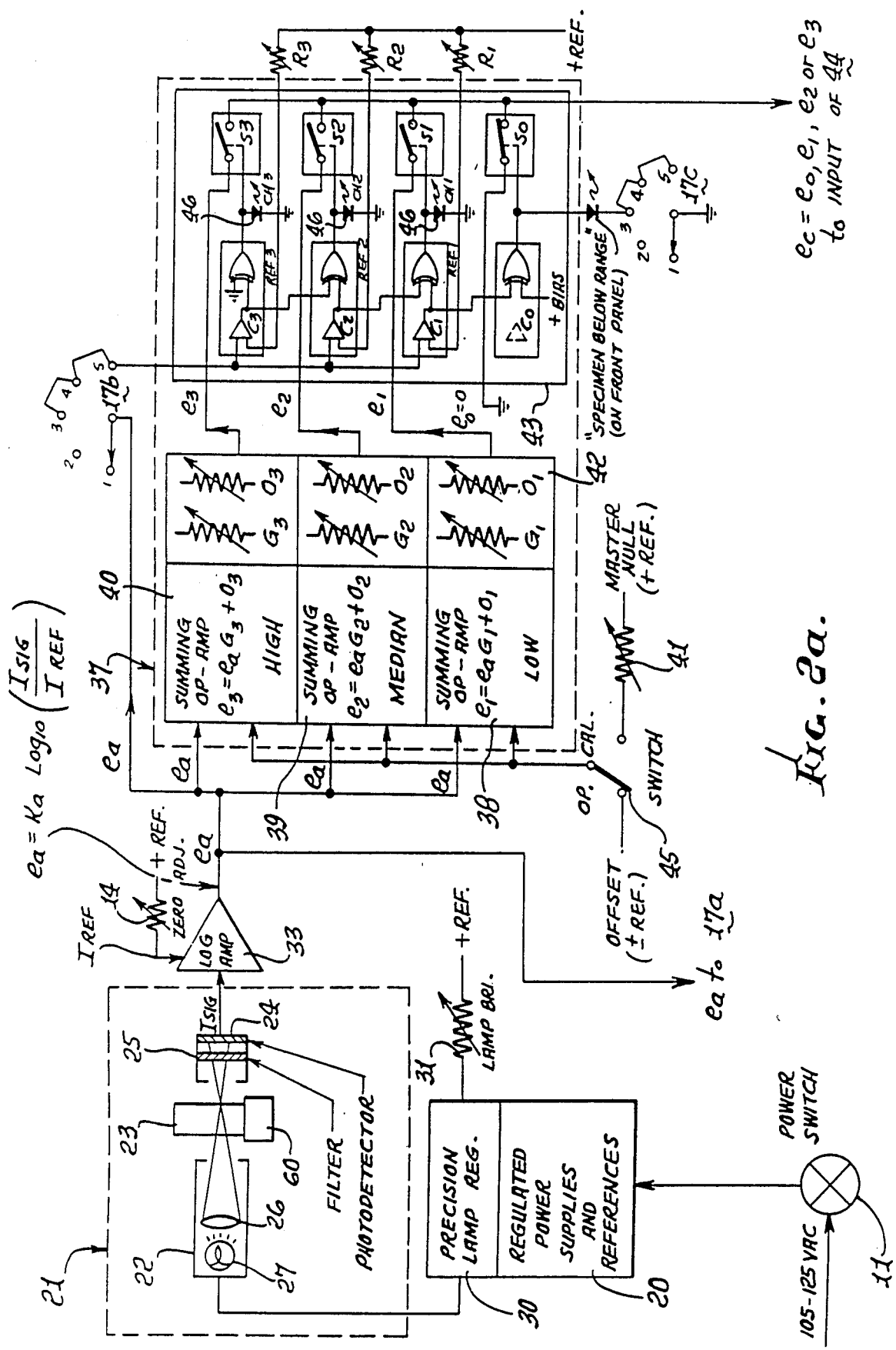
FIGS. 2A and 2B comprise an electrical block diagram of the instrument of FIG. 1.

The front panel 10, as shown in FIG. 1, includes: an illuminated POWER switch 11; a specimen drawer 12; a 3½ digit LCD digital panel meter 13 for data display; a ten-turn ZERO ADJUST potentiometer 14 for cuvette standardization; a pair of digitalized thumbwheel switch assemblies 15, 16 for dose computer entry of PERCENT MOTILITY and MILLION CELLS FOR INSEMINATION; and a FUNCTION selector switch 17. The FUNCTION selector has five positions: STANDBY; ZERO for cuvette standardization; COUNT to display the sperm density in millions of cells per milliliter; LOCK COUNT to hold the count readout for reference; and DOSE to provide entry of count into the dose computer and display the computed insemination dose in milliliters.

Block Diagram

Figure 2B:
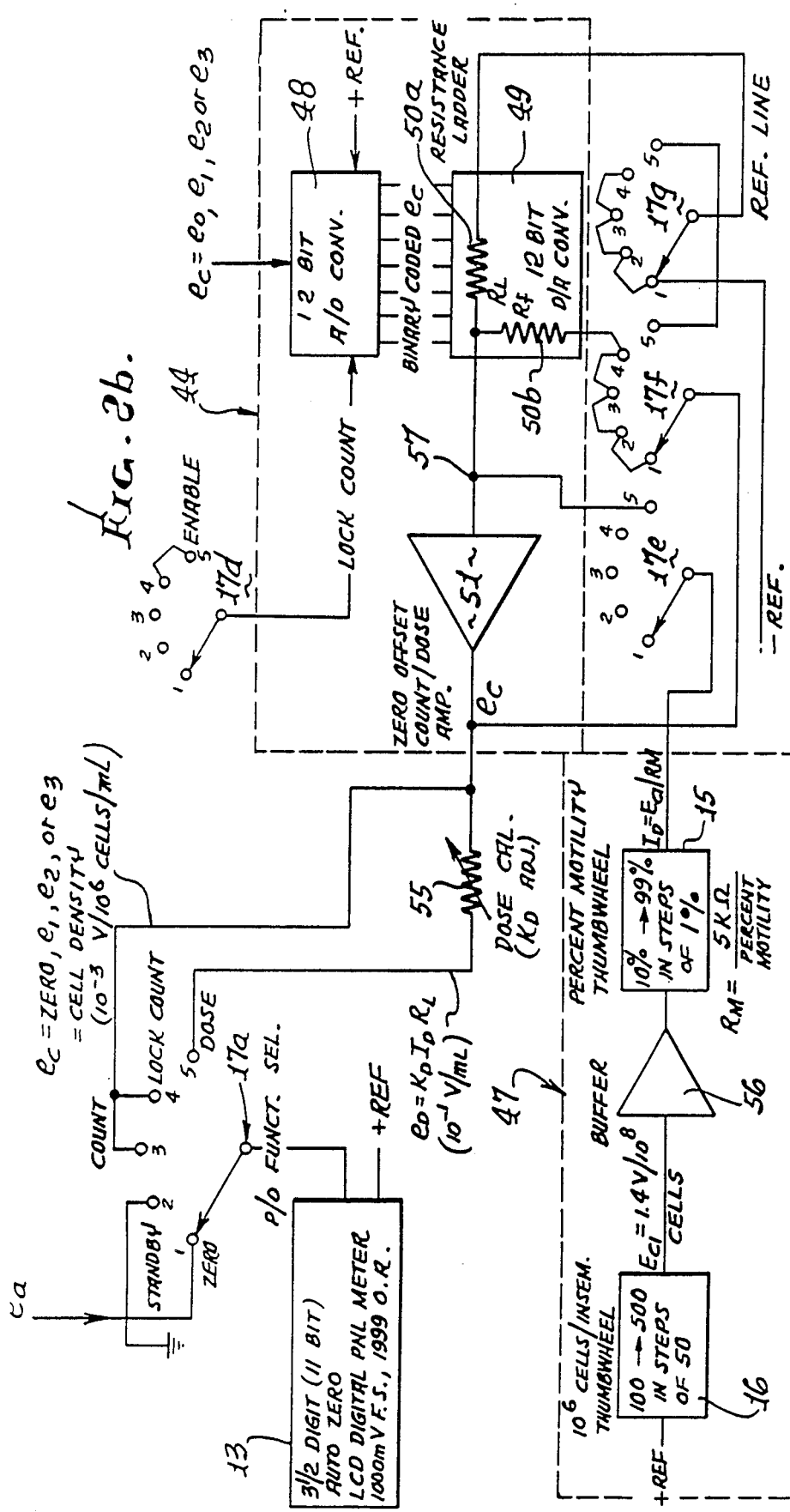

The internal opto-electronic system of the instrument of the invention is shown in the block diagram of FIG. 2.

Power Supply

The main power supply 20, which may be conventional in design, uses transformer-driven bipolar full wave rectification followed by capacitive-input filters. Several integrated circuit regulators are used to develop a number of stable dc potentials for use throughout the system. These include ±15 volt outputs for various operational amplifier circuits, ±5 volt outputs to energize the digital panel meter and an A/D converter in the COUNT/DOSE computer circuitry, and a separate +5 volt output for a logic gate system which is part of a multi-channel calibration system.

The power supply also includes bipolar precision master voltage reference outputs which supply time and temperature stable reference voltages of ±7 volts to a number of circuits.

Panel Meter

The LCD digital panel meter 13 is designed around a special integrated circuit which contains an 11-bit bipolar auto-zero dual integrating analog to digital (A/D) converter and a 3½ digit LCD display driver in a single 40-pin DIP. The meter circuit is powered from the ±5 volt output of the main power supply. A one volt reference potential supplied to the A/D converter sets a meter sensitivity of 35 1000 mv with 100% over range capability. The reference is developed by a precision voltage divider fed from the +7 volt reference output of the power supply.

The input to the panel meter is taken from various points during operation of the densimeter, as determined by the position of the FUNCTION switch 17, which has a plurality of decks 17a–17g. During cuvette standardization, the panel meter is used as a ZERO or null indicator. Later, it is used to display COUNT (sperm density) followed by DOSE. As a convenient feature, the bit generated by the A/D converter when a negative input is applied is connected to cause display of decimal point $D_2$ (to the left of the second most significant digit) rather than to display the usual negative symbol (−). This causes the decimal point to automatically appear in the proper position when reading DOSE, because this signal is of negative polarity. As required, the decimal point does not appear when positive inputs from the COUNT circuit are applied. In addition, this feature provides a true null indication (midway between ±001) during cuvette standardization when adjustment is made to cause the decimal point to just appear, because the IC incorporates very accurate auto-zero circuitry.

Additional components on the meter board establish the clock frequency and time constant of the integrator, which are set to maximize rejection of 50/60 Hz noise and to optimize conversion linearity.

Optical Assembly

The optical assembly 21 includes a projection lamp-lens assembly 22, a specimen cuvette holder 60 shown with cuvette 23 and a shrouded optically filtered silicon photodetector 24. The projection lamp-lens assembly produces a broad spectrum beam of radiant energy which impinges on the silicon photodetector after passage through the specimen cuvette and an optical band-pass filter 25. An aspheric lens 26 efficiently gathers light from the incandescent lamp filament 27 and forms a sharply focused image of the filament at the entry port of the photodetector shroud when clear (transparent) diluent is in the cuvette 23. Located beyond the focal point, the photodetector receives a defocused filament image which covers a large portion of the detector surface area.

The optical band-pass filter 25 is located in the photodetector housing. The filter has a photopic response which peaks broadly at 555 nm and limits reception of radiant energy at the photodetector to the range of approximately 400 nm to 700 nm (the visible spectrum). This broad band width system utilizes a relatively large portion of the energy produced by the projection lamp and allows a tremendous reduction in the power rating of the lamp compared to that needed in narrow band spectrophotometers. This greatly reduces heat generation, simplifies the lamp power supply, improves brightness stability and allows rating the projection lamp for a minimum life of 50,000 hours.

The silicon photodetector is operated essentially on short circuit and at a maximum output current which is a tiny percentage of the saturation current level. A study of silicon photodetector characteristics reveals that under these conditions, the current is a linear function of the level of illumination. When a standard quantity of semen is mixed with the measured volume of diluent in the specimen cuvette, the mixture becomes turbid to a degree dependent upon the sperm concentration. This reduces the amount of light reaching the photodetector and causes a corresponding reduction in the photodetector output current relative to the value established at standardization with clear diluent. As will be shown, it is this change in photodetector current which, after processing, yields a potential having numerical equality in millivolts with the sperm density in millions of cells per milliliter. The description of signal processing will continue under the paragraph entitled Log Amplifier which follows a general discussion of the optical system and specifics on the lamp regulator.

It is important to note that when photoelectric measurements of transmission or absorbance are made through a turbid or translucent medium, considerably greater differences in the measured value will occur between instruments of various design than when measuring a medium that produces little or no scattering of light. When scatter occurs, instruments allowing large amounts of scatter to reach the photodetector will show smaller changes in output current than those having photodetectors with more limited viewing angle.

Within a design, those factors affecting viewing angle (such as physical spacing between specimen and photodetector, photodetector surface area, position of photodetector shroud, size of shroud aperture, etc.) must be carefully maintained in production in order to achieve correlation amongst instrument readings. In the case of the densimeter, minor fixed variations in the viewing angle from instrument to instrument can be compensated by adjustment of versatile calibration circuitry. Obviously, however, all components within the optical system must be solidly mounted and the cuvette holder and drawer assembly must be capable of precisely maintaining the closed-drawer position of the cuvette in order to achieve excellent measurement correlation and repeatability with a controlled viewing angle for the detector.

Lamp Regulator

The precision lamp regulator 30 provides an internally adjustable constant current to the projection lamp 27. The value of delivered current must be stable over a practical range of environmental temperatures and must be independent of line voltage changes over the specified range. The required degree of regulation is very high because lamp brightness is quite sensitive to small changes in filament current. The dc input power to the regulator is provided by the power supply 20.

A natural degree of current regulation is provided by the use of a MOSFET in the regulator, through selection of an operating point that is well into its characteristic constant current region. The equivalent large dynamic series impedance of the MOSFET is enhanced by action of a high gain current error amplifier. The lamp current is adjusted at calibration by means of an internal potentiometer 31 which sets the reference voltage applied to an error amplifier of the regulator.

Log Amplifier

The logarithmic amplifier 33 which is driven by the photodetector 24, produces an output potential that is proportional to the absorbance of the specimen. The log amplifier may be a commercial module which uses the logarithmic relationship between the emitter-base voltage of transistors and their collector current in a feedback configuration to produce the desired logarithmic gain characteristic. The unit selected is capable of tracking the log function over six decades with an error of less than 1%. As used in the densimeter, it is exercised through a range of less than two decades.

A stable reference current, $I_{ref}$, is internally generated and may be trimmed by external injection from a stable adjustable supply. This is accomplished in the densimeter by adjustment of the 10-turn ZERO ADJUST panel potentiometer 14 which is fed from the power supply. The gain of the amplifier, Ka, may be set by pin selection and/or external resistors and is adjusted to a value of 2 for use in the densimeter.

The output of the photodetector $I_{sig}$ is connected directly to the amplifier input. Because the input ties to the summing junction of an inverse feedback op-amp circuit, it is at virtual ground potential. This places the photodetector on short circuit as required to provide linear opto-current conversion. Thus the value of $I_{sig}$ delivered by the photodetector when semen has been mixed with the diluent, expressed as a percentage of the value of $I_{sig}$ with pure diluent, is equal to the percent transmission. The output voltage of the log amplifier is given by the expression:

$$e_a = -Ka \, \mathrm{Log}_{10} \frac{I_{sig}}{I_{ref}}$$

This is a direct conversion of transmission, represented by the change that occurs in $I_{sig}$ when semen is mixed with the diluent, to an absorbance-proportional potential $e_a$, providing $I_{ref}$ has been set equal to $I_{sig}$ during standardizization of the cuvette prior to the addition of semen. As noted, $I_{ref}$ is set equal to $I_{sig}$ with the ZERO ADJUST panel control. Equality is indicated by a null on the panel meter when the FUNCTION switch is in the ZERO position.

During initial factory adjustments, the ZERO panel control is set to mid range with a representation of a nominal diluent-filled cuvette installed. The internal lamp brightness control is then set to null the output of the log amplifier, indicating a match of $I_{sig}$ to the median value of the available range of $I_{ref}$.

Because of the sensitivity of the log amplifier to minor supply voltage changes, a set of on-board voltage regulators are provided. These produce an output of ±12 volts, fed from the ±15 volt system and provide a high degree of stability.

Calibration Section

The calibration section 37 is designed to provide compensation for non-linearity between absorbance and sperm density. The compensation provides superior measurement accuracy over a wide range of sperm concentrations with the use of but a single diluent ratio. The calibration section also inserts scale factors which operate on the absorbance input signal to cause the displayed output to be numerically equal to sperm density in millions of cells per milliliter.

In general, the Calibration Section functions by delineating three absorbance signal magnitude ranges or segments corresponding to low, median and high sperm concentrations. The slope and vertical offset of each segment are independently adjusted (during calibration) so as to translate the input potential to a set of three sequentially selectable outputs which form contiguous segments having an average slope of 1 mv per million cells per milliliter, as required for proper numerical presentation of sperm density on the panel meter.

The calibration section consists of two major subsections; a tri-channel amplifier 42 and a channel selector 43. The tri-channel amplifier contains a bank of three high stability fractional gain op-amp circuits 38, 39, 40 having individual gain G (slope) and offset O calibration adjustments $G_1$, $G_2$, $G_3$, $O_1$, $O_2$, $O_3$. The amplifiers form three channels which are driven in parallel by the absorbance signal from the log amplifier 33 and make three processed outputs available for selection; $e_1 = e_a G_1 + O_1$, $e_2 = e_a G_2 + O_2$ and $e_3 = e_a G_3 + O_3$.

The channel selector 43 selects and transfers the output of the appropriate amplifier to the output section 44, when commanded by the FUNCTION switch 17b.

The channel selector 43 includes a four-section exclusive OR gate window comparator C0, C1, C2, C3 coupled to a set of four analog switches S0, S1, S2, S3 which provide grounded (zero) output or a transfer of signal $e_1$, $e_2$ or $e_3$ as required. The position and width of the segments are set by three calibration potentiometers R1, R2, R3. The potentiometers scale a stable voltage taken from the master reference for application as individual references to the three active channel comparators C1, C2 and C3.

The channel selector is enabled by parallel application of the absorbance signal $e_a$ to the three comparators C1, C2, C3. This occurs when the FUNCTION switch 17(b) is placed in the COUNT, LOCK COUNT or DOSE positions. The channel selected is dependent upon the magnitude of the absorbance signal $e_a$. The output of the channel selector 43 is held at ground potential by switch S0 unless a channel selection has been made. If a count is below the range of channel 1, the channel selector output will remain grounded when the FUNCTION switch is rotated to COUNT. The panel meter then displays zeros and the logic circuit allows the "SPECIMEN BELOW RANGE" panel LED to illuminate.

The OP-CAL switch 45 is used during calibration to temporarily remove the offset bias supply and insert a master nulling potential controlled by potentiometer 41. The nulling potential is used during calibration to zero each amplifier output at the bottom edge of its respective window. This allows the channel count range to be directly read on the panel meter 13 (eliminating the need to subtract readings) and removes all interaction between gain and offset calibration adjustments. Calibration is also expedited by three LED lamps 46 which provide visual indication that the desired channel has been activated.

The channel breakpoints and count-per-unit-absorbance values required for calibration are determined by statistical reduction of laboratory data. The data provides the absorbance, measured in a master densimeter, and corresponding duplicate hemocytometer or electronic counter measurements for a large number of semen samples covering a wide range of sperm concentrations.

Initial calibration and field testing and calibration of production units is accomplished using a set of five molded plastic calibration standards having sequential count values which have been verified by measurement in a master instrument. The first standard (clear) simulates a diluent-filled cuvette, the next three have densities corresponding to the desired count at each channel break point and the last has a density corresponding to the upper calibration point of range three.

Output Section

The analog signal from the calibration section 37 is coupled to the panel meter 13 through digital output circuitry 44 which is common to the dose computer 47. This provides a means for automatic entry of the density count C into the dose computer, provides excellent tracking between the DOSE and COUNT functions and allows implementation of the LOCK COUNT function.

The analog output $e_c$ of the calibration section is first converted to a binary code by a 12-bit dual integrating A/D converter 48. This has twice the resolution of the digital panel meter to assure maintenance of accuracy and system linearity. The one-volt reference for the A/D converter is derived from the master reference by a high stability resistive voltage divider.

The binary coded count signal from the A/D converter is fed directly to a complementary D/A converter 49 designed on the resistance ladder principle. In effect, a resistance value is established on the ladder 50a (RL) which is inversely proportional to the input count. When the FUNCTION switch 17e, f, g is in the COUNT mode, the computer input from the percent motility switch is disabled, and the D/A converter reference line is fed from the −7 volt output of the master reference. The resistance ladder 50a is connected as the input resistor of a conventional inverting mode feedback amplifier 51 with the feedback component being formed by a fixed resistor 50b (Rf) contained within the D/A converter 49. The amplifier 51, which is part of the D/A converter, is an op-amp having a high degree of temperature stability, very high input impedance (low bias current) and a laser-cut balance network to assure essentially zero offset voltage.

The reconstructed analog density count signal $e_c$ appearing at the output of the amplifier 51 is directly proportional to count because of the position of the ladder in the amplifier network (output potential is inversely proportional to input resistance, input resistance is inversely proportional to count) and in fact is identical to the input signal $e_c$ at A/D 48 because the D/A conversion is scaled to produce an overall gain of unity. As previously explained, the output potential in millivolts is equal to the count C in millions of cells per milliliter by virtue of adjustments made in the calibration section.

The output polarity of the amplifier 51 is positive because of the negative reference applied to the A/D converter and the ensuing polarity inversion that occurs in the amplifier.

In the LOCK COUNT mode of the FUNCTION switch 17d, a HOLD capability of the A/D converter is enabled which locks the binary code pattern at the output of the A/D converter. This allows maintaining the count for reference after the specimen cuvette has been removed and also allows re-examination of the count value entered into the dose computer 47.

Dose Computer

The dose computer 47 is an analog computer outfitted with automatic digital entry of COUNT data and manual stepped entry of million cells per insemination and percent motility via panel thumbwheel switches 16 and 15, respectively, which have digital readout dials.

Analog circuitry was chosen because it provides the advantages of rapid data entry and a hard-wire solution to the dose equation that completely eliminates the need for manipulation of mathematical functions. In addition, it provides a nearly instantaneous re-calculation of the dose by simply changing panel dial settings to match the requirements for individual inseminations.

A major disadvantage of analog computation is relative lack of precision compared with digital computation. This is irrelevant in this application because the maximum computational error exhibited is less than 1% which is considerably better than the accuracy with which the subjective percent motility estimate can be made.

When the FUNCTION selector 17 is rotated to DOSE, the digital COUNT/DOSE output circuitry is reconfigured by 17e, f, g in a number of ways. The LOCK COUNT function is maintained on the A/D converter hold pin to preserve the COUNT data represented on the D/A converter resistance ladder. However, the panel meter now reads the output of the COUNT/DOSE amplifier 51 through a dose calibration potentiometer 55 while the negative seven-volt reference and amplifier feedback resistor 50b are disconnected from the circuit. The D/A converter resistance ladder 50a is a lockable digitally selected resistance and is switched to take the position of amplifier feedback resistor 50b and the step-adjustable resistance of the percent motility thumbwheel 15 becomes the amplifier input resistor.

The inverting amplifier thus formed is driven by a buffer amplifier 56 from the output of the million cells per insemination stepped voltage divider 15 which is fed from the +7 volt output of the master reference.

The numerical constants shown on the block diagram are those for a stallion sperm counter and will be used to describe operation of the DOSE computer circuit. Recalling the insemination dose equation:

$$\text{DOSE} = \frac{\text{CELLS PER INSEMINATION}}{\text{COUNT} \times \text{MOTILITY}} = \frac{N}{CM}$$

it may be seen that the dose meter read-out must be made to be directly proportional to the selected value of cells per insemination.

For the equine, this value ranges between 100 million and 500 million in steps of 50 million, which is sufficient resolution for practical applications. The million cells per insemination thumbwheel 16 controls a stepped potentiometer consisting of nine precision resistors. With a potentiometer input of +7 volts, the output potential $E_{CI}$ ranges between 1.4 volts to 7.0 volts in steps of 0.7 volt per 50 million cells, which is representative of the required direct proportion.

In order to achieve the above-described linear step-changes, the resistance loading on the potentiometer must be very large compared to its characteristic resistance. This is provided by a high input impedance unity gain op-amp buffer 56 which also has excellent temperature stability and essentially zero voltage offset to preserve the integrity of the signal.

The output of the buffer amplifier 56 feeds a pair of stepped decade resistances 15 connected in tandem which provide for entry of the percent motility. Each decade utilizes a 1-2-2-2 switch code to allow establishing a total of 90 values (from 10% to 99% in 1% steps) with the use of only 10 precision resistors. The selected base is 5K ohms per percent motility so that the decade resistance value $R_M$ may range from 50K ohms to 495K ohms. Each side of the decade is terminated in a resistance which is very small compared to the minimum resistance of the decade. The input side is fed from the source impedance of the buffer which is less than 1 ohm. The output side feeds into the summing junction 57 of the inverse feedback amplifier 51, which is virtually at ground potential. The input current $I_D$ fed to the amplifier summing junction, then, is inversely proportional to the resistance $R_M$ established by the Percent Motility dial and directly proportional to the voltage $E_{CI}$ established by the Million Cells Per Insemination dial. Because the output voltage of the amplifier is directly proportional to the input current, it follows that the output voltage of the amplifier will accurately reflect the panel thumb wheel settings in accordance with the requirement of the dose equation.

The remaining parameter is the automatically entered COUNT established as a resistance value on the D/A converter resistance ladder. The resistance ladder is connected as the feedback resistance of the amplifier 51. The output voltage of the amplifier is directly proportional to the value of the feedback resistor, but recalling that the value of resistance established on the ladder is inversely proportional to COUNT, it follows that the output is also inversely proportional to COUNT, which again matches the requirement of the dose equation.

Two things remain to be accomplished. First, a proportionality factor must be established so that the voltage delivered to the panel meter is numerically equal in decivolts to the DOSE in milliliters. This is done by the calibration potentiometer 55 which establishes a value of 0.100 volt per 1.00 milliliter. Second, a decimal point must be displayed in the proper position. This is automatically accomplished simply by the use of the positive reference input to the DOSE computer. Inversion of this signal to negative polarity by the amplifier 51 causes the panel meter to display a decimal point in the correct position. The maximum dose that can be displayed is 19.99 ml. The volume of semen used for insemination of mares seldom exceeds 10 ml.

By way of summary of the count and compute functions, when in the Density Count mode there are two inputs to the D/A converter 49; a lockable 12-bit digital code from the A/D converter 48 which sets the value of the resistance ladder, and a stable DC reference which drives the amplifier 51 to provide the analog Density Count output. Calibration of this first output is accomplished in the calibration section 37 so that the first output is directly the first input available to the display meter 13.

When in the Dose mode, the amplifier 51 utilizes the resistance ladder of the D/A converter. The locked resistance value (representative of the just-completed Density Count measurement) is transferred to become the feedback element of the amplifier to provide the required ratio-to-count function. In this mode, the amplifier summing junction 57 is driven by the output current $I_D$ from the dose computer circuit 47. The amplifier 51 now provides a second, different output which is the dose signal for the display meter 13.

Specimen Drawer

The lamp-lens assembly 22, the filter 25 and the photodetector 26 are mounted in the housing behind the front panel 10. The cuvette 23 is carried in a cuvette holder 60 of the specimen drawer 12, shown in more detail in FIG. 3. The specimen drawer includes a bottom plate 61 with a front 62 and handle 63 attached to the bottom plate by screws 64. The holder 60 is attached to a support post on the base 61 by rivets 65. Two springs 66 are provided in the holder to snugly hold the cuvette in a fixed and repeatable position. Appropriate guides and latches may be provided on the drawer as desired.

Typical Operating Procedure

1. Plug power cord into any grounded 115 volt ac outlet. Rotate FUNCTION selector 17 to STANDBY and POWER switch 11 to ON. Allow 5 minutes for warm-up before using instrument.
2. Pipette exactly 3.42 milliliters of clear diluting fluid into a fresh cuvette 23, then cover with snap-on cap. Examine inner surfaces of cuvette for presence of bubbles and dislodge any that have formed by gently tilting and rotating the cuvette.
3. Clean outer surfaces of cuvette with disposable wiper and install into drawer 12 with either of the ribbed sides facing the operator.
4. Rotate FUNCTION selector 17 to ZERO.
5. Standardize cuvette by setting the ZERO ADJUST knob 14 for a reading of 000 on the digital display. Make final adjustment by turning knob counter clockwise until decimal point just appears 0.00.
6. Return FUNCTION selector 17 to STANDBY.
7. Add exactly 0.18 milliliters of raw gel-free semen to the standardized cuvette. Replace cuvette cap and obtain a homogeneous bubble-free mix by gently tilting and rotating the cuvette at least ten times. Clean outer surfaces of cuvette and reinstall into drawer.
8. Rotate FUNCTION selector 17 to COUNT. Digital display indicates sperm density in millions of cells per milliliter.
9. Rotate FUNCTION selector 17 to LOCK COUNT.
    a. Enter the estimated progressive motility on the percent motility dial 15.
    b. Enter the total number of motile sperm cells desired for insemination on the millions cells per insemination dial 16.
    c. Rotate FUNCTION selector 17 to DOSE. Digital display indicates the computed insemination dose or volume of raw semen to be used for insemination in milliliters.

We claim:

1. A method of measuring density of sperm in a sample, including the steps of:
    measuring the optical absorbance of a diluent-filled cuvette to obtain a measured output and adjusting the measured output to a null for standardizing the measurement;
    measuring the optical absorbance of a sample specimen to provide an analog absorbance signal which varies as a function of sperm density in the sample specimen;
    providing said analog absorbance signal as input to at least three summing channels as summing signals defining a line having slope and vertical offset;
    changing the slope and vertical offset of each of said summing signals by multiplying the summing signal by a first amount and adding a second amount to the product, to provide changed signals;
    determining the level of said analog absorbance signal and selecting one of said changed signals as a selected analog output signal; and
    displaying the selected analog output signal as a direct indication of density.

2. The method as defined in claim 1 including measuring optical absorbance in the range of 400 to 700 nanometers.

3. The method as defined in claim 1 including measuring optical absorbance in a wide band visible spectrum.

4. The method as defined in claim 3 including focusing a light source through the sample specimen and defocusing the light source at a detector, with the detector having a controlled viewing angle for receiving scattered light from the sample specimen.

5. The method as defined in claim 1 including:
setting a cell number;
setting a percent motility figure; and
determining a dose by calculating the percent motility number divided by the product of the selected analog output signal and the figure.

6. The method as defined in claim 1 including:
setting a voltage as a portion of a reference voltage to be directly proportional to insemination cell number;
setting a resistance to be directly proportional to percent motility and driven by said voltage proportional to insemination cell number to provide a current signal directly proportional to insemination cell number and inversely proportional to percent motility;
feeding said current signal to the summing point of an operational amplifier utilizing a feedback element comprised of a digitally selected resistance locked to a value functionally related to previously measured density count so as to develop an amplifier output potential directly proportional to insemination cell number and inversely proportional to density count and percent motility;
and calibrating said amplifier output potential to provide display of a dose number in milliliters.

7. The method as defined in claim 1 including:
setting a voltage as a portion of a reference voltage to be directly proportional to insemination cell number;
setting a resistance to be directly proportional to percent motility;
driving said resistance by said voltage to provide a current signal directly proportional to insemination cell number and inversely proportional to percent motility;
feeding said current signal to the summing point of an operational amplifier utilizing as a feedback element, a digitally selected resistance locked to a value functionally related to the measured density count;
calibrating said amplifier output potential to provide display of a dose number in milliliters.

* * * * *